United States Patent
Bratbak

(10) Patent No.: US 12,220,178 B2
(45) Date of Patent: Feb. 11, 2025

(54) METHOD AND APPARATUS FOR CALIBRATING AN INSTRUMENT FOR SURGICAL INTERVENTION

(71) Applicant: Norwegian University of Science and Technology (NTNU), Trondheim (NO)

(72) Inventor: Daniel Fossum Bratbak, Trondheim (NO)

(73) Assignee: Norwegian University of Science and Technology (NTNU), Trondheim (NO)

( * ) Notice: Subject to any disclaimer, the term of this patent is extended or adjusted under 35 U.S.C. 154(b) by 610 days.

(21) Appl. No.: 17/272,451

(22) PCT Filed: Sep. 13, 2019

(86) PCT No.: PCT/EP2019/074555
§ 371 (c)(1),
(2) Date: Mar. 1, 2021

(87) PCT Pub. No.: WO2020/053421
PCT Pub. Date: Mar. 19, 2020

(65) Prior Publication Data
US 2021/0322107 A1    Oct. 21, 2021

(30) Foreign Application Priority Data
Sep. 13, 2018    (GB) .................................... 1814924

(51) Int. Cl.
*A61B 34/20*    (2016.01)
*G06T 7/73*    (2017.01)
*A61B 17/00*    (2006.01)

(52) U.S. Cl.
CPC ................ *A61B 34/20* (2016.02); *G06T 7/73* (2017.01); *A61B 2017/0023* (2013.01);
(Continued)

(58) Field of Classification Search
CPC ............ A61B 34/20; A61B 2034/2055; A61B 2090/3983; A61B 2017/00725
See application file for complete search history.

(56) References Cited

U.S. PATENT DOCUMENTS

| | | |
|---|---|---|
| 4,886,493 A | 12/1989 | Yee |
| 5,766,605 A | 6/1998 | Sanders et al. |

(Continued)

FOREIGN PATENT DOCUMENTS

| | | |
|---|---|---|
| CN | 105055021 A | 11/2015 |
| DE | 202007004191 U1 | 6/2007 |

(Continued)

OTHER PUBLICATIONS

Piagkou M N et al: "The Pterygopalatine Ganglion and its Role in Various Pain Syndromes: From Anatomy to Clinical Practice", EMBASE, Jun. 1, 2012 (Jun. 1, 2012), XP002717711, the whole article.

(Continued)

*Primary Examiner* — Jason M Ip
(74) *Attorney, Agent, or Firm* — Banner & Witcoff, Ltd.

(57) ABSTRACT

A method of calibrating an instrument for surgical intervention is provided. The instrument to be calibrated has a tip at a distal end thereof and a navigation array that is spaced from the distal end and is detectable in space. The navigation array has a fixed spatial and angular relationship with the tip. The method comprises the steps of: placing a calibrator on the tip of the instrument such that the tip is positioned within the calibrator at a known displacement from the centre of the calibrator, the calibrator having a circular shape and being detectable as a single point in space; detecting the position of the navigation array and the centre of the calibrator; and determining the position of the centre of the calibrator relative to the navigation array, thereby calibrating the position of the tip of the instrument relative to the navigation (Continued)

array. There is also provided a calibrator for use in such a method.

24 Claims, 3 Drawing Sheets

(52) U.S. Cl.
CPC ............... *A61B 2017/00725* (2013.01); *A61B 2034/2055* (2016.02); *G06T 2207/10048* (2013.01)

(56) References Cited

U.S. PATENT DOCUMENTS

| | | | |
|---|---|---|---|
| 6,021,343 | A | 2/2000 | Foley et al. |
| 6,322,542 | B1 | 11/2001 | Nilson et al. |
| 6,351,659 | B1 | 2/2002 | Vilsmeier |
| 6,491,940 | B1 | 12/2002 | Levin |
| 6,497,134 | B1 | 12/2002 | Faul et al. |
| 7,155,316 | B2 | 12/2006 | Sutherland et al. |
| 7,166,114 | B2 | 1/2007 | Moctezuma De La Barrera et al. |
| 7,419,497 | B2 | 9/2008 | Muni et al. |
| 7,725,162 | B2 | 5/2010 | Malackowski et al. |
| 7,799,337 | B2 | 9/2010 | Levin |
| 7,896,838 | B2 | 3/2011 | Devega |
| 7,981,433 | B2 | 7/2011 | Blumenfeld |
| 8,123,697 | B2 | 2/2012 | Daum et al. |
| 8,231,588 | B2 | 7/2012 | Xia |
| 8,388,600 | B1 | 3/2013 | Eldredge |
| 8,795,188 | B2 | 8/2014 | Maschke |
| 8,846,622 | B2 | 9/2014 | Blumenfeld |
| 9,060,794 | B2 | 6/2015 | Kang et al. |
| 9,364,230 | B2 | 6/2016 | Shelton, IV et al. |
| 9,622,832 | B2 | 4/2017 | Birkenbach et al. |
| 2002/0016599 | A1 | 2/2002 | Kienzle et al. |
| 2003/0208122 | A1 | 11/2003 | Melkent et al. |
| 2004/0068179 | A1 | 4/2004 | Jutras et al. |
| 2004/0219478 | A1 | 11/2004 | Harter |
| 2005/0020909 | A1 | 1/2005 | Moctezuma de la Barrera et al. |
| 2005/0154296 | A1 | 7/2005 | Lechner et al. |
| 2005/0267009 | A1 | 12/2005 | Deagle |
| 2006/0063973 | A1 | 3/2006 | Makower et al. |
| 2006/0104707 | A1 | 5/2006 | Neubauer et al. |
| 2006/0171963 | A1 | 8/2006 | Blumenfeld |
| 2006/0281991 | A1 | 12/2006 | Fitzpatrick et al. |
| 2007/0167868 | A1 | 7/2007 | Sauer |
| 2007/0173790 | A1 | 7/2007 | Moctezuma De La Barrera et al. |
| 2007/0208252 | A1 | 9/2007 | Makower |
| 2007/0250105 | A1 | 10/2007 | Ressemann et al. |
| 2008/0103509 | A1 | 5/2008 | Goldbach |
| 2008/0161679 | A1 | 7/2008 | von Jako et al. |
| 2008/0185430 | A1 | 8/2008 | Goldbach |
| 2008/0249500 | A1 | 10/2008 | Keith et al. |
| 2008/0279895 | A1 | 11/2008 | Blumenfeld |
| 2009/0012532 | A1 | 1/2009 | Quaid et al. |
| 2009/0192408 | A1 | 7/2009 | Mark |
| 2009/0318875 | A1 | 12/2009 | Friedman |
| 2010/0030187 | A1 | 2/2010 | Xia |
| 2010/0030188 | A1 | 2/2010 | Xia |
| 2010/0049230 | A1 | 2/2010 | Benary et al. |
| 2010/0100081 | A1 | 4/2010 | Tuma et al. |
| 2010/0227822 | A1 | 9/2010 | Blumenfeld |
| 2011/0295263 | A1* | 12/2011 | Nishio .................. A61B 34/20 606/96 |
| 2012/0316486 | A1 | 12/2012 | Cheung et al. |
| 2013/0060278 | A1 | 3/2013 | Bozung et al. |
| 2013/0087152 | A1 | 4/2013 | Kirn |
| 2013/0130193 | A1 | 5/2013 | Fisher et al. |
| 2013/0218142 | A1 | 8/2013 | Tuma et al. |
| 2014/0357982 | A1* | 12/2014 | Malul .................. A61C 3/025 606/167 |
| 2015/0182293 | A1 | 7/2015 | Yang et al. |
| 2015/0265769 | A1* | 9/2015 | Bratbak .................. A61M 5/28 604/95.01 |

FOREIGN PATENT DOCUMENTS

| | | |
|---|---|---|
| EP | 345975 A2 | 12/1989 |
| EP | 1444962 A2 | 8/2004 |
| EP | 1915962 A1 | 4/2008 |
| EP | 2179703 A1 | 4/2010 |
| IN | 105919669 A | 9/2016 |
| WO | 2004075768 A2 | 9/2004 |
| WO | 2005000139 A1 | 1/2005 |
| WO | 2005120380 A1 | 12/2005 |
| WO | 2006/118915 A2 | 11/2006 |
| WO | 2008091917 A2 | 7/2008 |
| WO | 2009107703 A1 | 9/2009 |
| WO | 2010/061124 A1 | 6/2010 |
| WO | 2011084507 A1 | 7/2011 |
| WO | 2013/192501 A1 | 12/2013 |
| WO | 2014/037524 A1 | 3/2014 |
| WO | 2016141378 A1 | 9/2016 |

OTHER PUBLICATIONS

Slades G et al: "Control of lacrimal secretion after sphenopalatine ganglion block" Ophthalmic Plastic and Reconstructive Surgery, Masson, New York, NY, US, vol. 2, No. 2, Jan. 1, 1986 (Jan. 1, 1986), pp. 65-70, XPO09174933, ISSN: 0740-9303, figure 2, abstract, rest of article.

Varghese et al., Endoscopic transnasal neurolytic sphenopalatine ganglion block for head and neck cancer pain, The Journal Of Larygology & Otology, May 2001, vol. 115, pp. 385-387.

Olesen, The role of nitric oxide (NO) in migraine, tension-type headache and cluster headache, Pharmacology & Therapeutics, 120 (2008) 157-171.

Cohen et al., Functional neuroimaging of primary headache disorders, Expert Rev. Neurotherapeutics, 6(8), (2006), 1159-1171.

Maizels et al., Intranasal Lidocaine for Migraine: A Randomized Trial and Open-Label Follow-up, Headache, 1999; 39(8):543-51.

Cassano et al., Sphenopalatine artery ligation with nerve resection in patients with vasomotor rhinitis and polyposis: a prospective, randomized, double-blind investigation, Acta Oto-Laryngologica, 2012;132(5):525-32.

Goadsby, Pathophysiology of cluster headache: a trigeminal autonomic cephalgia, Lancet Neurology, 2002;1:251-57.

Goadsby et al., Trigeminal automomic cephalagias: diagnostic and therapeutic developments, Current Opinion in Neurology, 2008;21:323-330.

Maizels et al., Intranasal lidocaine for treatment of migraine: a randomized, double-blind, controlled trial, JAMA, 1996;276(4):319-21.

Su et al., Antegrade transsphenoidal vidian neurectomy: Short-term surgical outcome analysis, American Journal of Rhinology & Allergy, 2011;25:e217-e220.

Yang et al., A novel approach to transnasal sphenopalatine ganglion injection, MEDLINE abstract Accession No. NLM16703973, Pain Physician, vol. 9, No. 2, 2006, pp. 131-134.

Turk et al., Botulinum toxin and intractable trigeminal neuralgia, Clinical Neuropharmacology, vol. 28, No. 4, 2005, pp. 161-162.

Felisati G. et al., Sphenopalatine Endoscopic Ganglion Block, The Laryngoscope 116(8)1447-50, Aug. 2006.

Miles Day, Sphenopalatine ganglion analgesia, Current Review of Pain, vol. 3, No. 5, Oct. 1, 1999 (Oct. 1,1999), pp. 342-347, XP055287005, US, ISSN: 1069-5850, DOI: 10.1007/s11916-999-0029-6.

Feb. 14, 2019 (GB) Search Report IPO Application No. GB1814924.5.

Jan. 15, 2020 (WO) International Search Report & Written Opinion Application No. PCT/EP2019/074555.

Search Report mailed Jun. 1, 2015 (GB1422551.0); IPO.

International Search Report and Written Opinion mailed Mar. 3, 2016 (PCT/EP2015/079989); ISA/EP.

\* cited by examiner

METHOD AND APPARATUS FOR CALIBRATING AN INSTRUMENT FOR SURGICAL INTERVENTION

RELATED APPLICATIONS

This application is a National Stage Application under 35 U.S.C. 371 of PCT application PCT/EP2019/074555 designating the United States and filed Sep. 13, 2019; which claims the benefit of GB application number 1814924.5 and filed Sep. 13, 2018 each of which are hereby incorporated by reference in their entireties.

The invention relates to a method of calibrating an instrument for surgical intervention and an associated apparatus and system.

The use of image guided surgical navigation systems to assist surgeons in performing delicate and precise surgery has become commonplace. Typically, image guided surgical interventions are employed where the precise and accurate positioning of a surgical instrument is of paramount importance. Image guided surgery is used to assist in orientation by displaying the position of a surgical instrument on a medical image. Armless systems may be based on light, sound waves or magnetic fields. With the use of a computer platform and a surgical navigation system, the position of a surgical instrument can be displayed to a user.

In many image guided surgical interventions, it is a requirement that, prior to commencement, the position of the tip of the surgical instrument is known to the surgical navigation system so as to allow the user to precisely guide the tip of the instrument into a desired site in the patient. Thus, a calibration of the tip of the instrument relative to the navigation system is required. Instruments may be calibrated by the manufacturer in advance of their use. However, even the slightest knock or damage to the instrument after the manufacturer's calibration, during use, transit or otherwise, can cause a deviation from the calibrated alignment of the instrument which, given the precision requirements, can render the instrument as unusable. Thus, it is preferred that a calibration of the instrument be carried out by the user each time prior to its use to ensure that the highest levels of precision and accuracy can be achieved during image guided surgery.

One such device that allows for the user calibration of a surgical instrument prior to its use is outlined in CN 105919669 A. The disclosed calibration device comprises a substrate having three optically active balls irregularly spaced thereon. The substrate is also provided with a plurality of semi-circular grooves of differing diameter that terminate at a known point on the substrate, each groove configured to receive a tip (e.g. a thin needle) of a surgical instrument. The termination point of each of the grooves relative to the position of the three optically active balls is calibrated by the manufacturer of the device and is therefore known.

The surgical instrument is calibrated by inserting the tip of the instrument into the appropriate groove on the calibration device (chosen based on the size of the instrument) until the tip of the instrument abuts the termination point, at which time the position of the tip of the surgical instrument is known relative to the three optically active spheres in the calibration device. Thus, by detecting the position of the three optically active spheres on the calibration device, the position of the surgical instrument's tip can also be detected, which in turn can be calibrated relative to a navigation array disposed on the surgical instrument.

Whilst calibration devices of the type outlined in CN 105919669 A allow for the calibration of a tip of a surgical instrument, these devices have certain drawbacks associated with them. For instance, as described above, calibration with the disclosed device requires the insertion of the tip of the instrument into one of the grooves provided on the substrate. Given the delicate and fragile nature of many of the surgical instruments used in image guided surgery (e.g. a thin needle or long forceps), even the slightest misplacement of the instrument relative to the calibration device can cause damage to the instrument, thus rendering the instrument as unusable.

Further, the calibration device itself must be calibrated, typically by the manufacturer, before it can be used to calibrate a surgical instrument. Thus, as with pre-calibrated surgical instruments, the slightest damage to the calibration device, during transit or otherwise, can cause a deviation from the calibrated alignment of the optically active spheres relative to the termination points of the grooves, which can render the calibration device as unusable.

Additionally, particularly in view of the required precision with which they must be manufactured to, calibration devices of the type known from CN 105919669 A can be extremely costly to manufacture.

The calibration of the position of the surgical instrument using the calibration device of CN 105919669 A is an indirect calibration of the tip (i.e. the position of the tip is not detected directly). Indirect calibrations can lead to imprecise or inaccurate instrument calibrations due to a build-up of engineering tolerances and/or misalignments in the components of the calibration device. Moreover, this indirect calibration method is reliant on the steady placement of the calibration device relative to the navigation array on the surgical instrument. This can require a trained or practised hand and can often lead to long calibration times.

Furthermore, whilst a plurality of semi-circular grooves of differing diameters are provided in the calibration device in order to accommodate surgical instruments of different dimensions, only a finite number of grooves are provided and thus the calibration device can only be used with a finite number of surgical instruments.

Another such system and method for calibrating a surgical instrument is known from US 2007/0173790 A1. The system disclosed therein makes use of a universal tracking device to calibrate the position of the tip of a surgical instrument. To calibrate the tip, the universal tracking device is fixed to the surgical instrument such that the tracking device has a fixed spatial relationship with an axis of the tip of the surgical instrument. The tracking device comprises three LEDs emitting infrared radiation that allow for detection of the position of the universal tracking device. A reference tracking device, separate from the surgical instrument and the universal tracking device, is also disposed within the system, the reference tracking device comprising three LEDs comparable to those disposed on the universal tracking device, and a calibration point that, having already been calibrated accordingly by the manufacturer, has a known spatial relationship relative to the three LEDs on the reference tracking device.

The surgical instrument is calibrated by touching the tip of the instrument to the calibration point on the reference tracking device. As the location of the calibration point and the universal tracking device are known to the system (via detection of the six LEDs), the system can determine the location of the instrument's tip relative to the universal tracking device.

Thus, whilst some of the technical aspects differ, the system and method disclosed therein are broadly similar to the system and method disclosed in CN 105919669 A. Both these documents disclose indirectly calibrating the position of the tip of a surgical instrument via the detection of a device fixed relative to the surgical instrument and the detection of three optically active bodies fixed on a calibration device. As such, many of the drawbacks discussed above in relation to CN 105919669 A also apply equally to the systems and methods known from US 2007/0173790 A1.

Improved methods and systems for calibrating the position of a surgical instrument prior to use in image guided surgery are therefore needed.

According to a first aspect of the invention, there is provided a method of calibrating an instrument for surgical intervention, the instrument having a tip at a distal end thereof and a navigation array spaced from the distal end and being detectable in space, wherein the navigation array has a fixed spatial and angular relationship with the tip. The method comprises the steps of: placing a calibrator on the tip of the instrument such that the tip is positioned within the calibrator at a known displacement from the centre of the calibrator, the calibrator having a circular shape and being detectable as a single point in space; detecting the position of the navigation array and the centre of the calibrator; and determining the position of the centre of the calibrator relative to the navigation array, thereby calibrating the position of the tip of the instrument relative to the navigation array.

A circular shape as defined herein includes circles, cylinders and spheres. Thus, the calibrator may be spherical in shape and may hence be termed a calibrator sphere. Equally, the calibrator may be circular in shape and may hence be termed a calibrator circle.

The calibrator used in the method of the first aspect requires no calibration prior to its use in calibrating the position of the tip of the surgical instrument. Thus, there is less risk of the calibrator being damaged in transit or in use than the calibration devices known from the prior art. The absence of prior calibration also means that the calibrator may be manufactured more cheaply than calibration devices known from the prior art, and is more readily usable as there is no need for the user to be trained in how to calibrate the instrument.

Further, as the calibrator is placed only on the tip of the surgical instrument, and since it may be relatively lightweight, the risk of any potential damage to the surgical instrument can be reduced.

The step of placing the calibrator on the tip of the instrument may comprise placing the calibrator firmly on the tip of the instrument. This allows the calibrator to be maintained in place on the tip of the instrument under the action of its own engagement with the instrument. As such, there is no requirement for the calibrator to be held in place on the tip by an operative and/or by additional retention means in order to keep the calibrator steady during calibration since the position of the calibrator can be fixed relative to both the surgical instrument and the position of the navigation array under its own engagement therewith. This is advantageous, particularly in the case where the calibrator is relatively lightweight, since damage to or bending of the instrument that may otherwise be caused from an operative having to hold the calibrator on the instrument during a calibration thereof can be avoided.

The present method is reliant on the detection of only a single entity (i.e. the calibrator) relative to a navigation array. Therefore, faster calibration of the surgical instrument can be achieved. Moreover, the step of calibration is simplified as the position of only one point in space (i.e. the calibrator) has to be determined relative to a navigation array.

The method of the first aspect may also allow for a more precise calibration of the tip of the surgical instrument as any errors in the calibration of the tip of the surgical instrument will be confined to errors that arise from the manufacturing tolerances in the calibrator and/or the incorrect placement of the calibrator on the tip of the surgical instrument. In contrast, calibration devices known from the prior art are reliant on a greater number of components (e.g. three optically active spheres and a substrate). Thus, the build-up in engineering tolerances of these component parts, in addition to any potential misplacement of the calibration device, can lead to a more imprecise calibration than that which is achieved with the method of the first aspect.

Thus, by means of the proposed method, the tip of an instrument for surgical intervention can be calibrated in a fast, precise and simple manner in view of its reliance on the detection of only a single entity relative to a navigation array.

After the tip of the instrument has been calibrated using the method of the first aspect, the method may optionally extend to the steps of removing the calibrator from the tip of the instrument, calculating a position of the tip of the instrument by detecting the position of the navigation array and displaying a position of the tip of the instrument to a user, such as to a surgeon during image guided surgery. Any suitable display means may be used to display the tip of the instrument to the user, though it is preferably a visual display, such as an LCD screen.

The tip of the instrument may be placed at any known displacement from the centre of the calibrator whilst positioned therein. However, it is preferred that the tip of the instrument is received within the centre of the calibrator such that the detection of the position of the centre of the calibrator allows for the simultaneous, direct detection of the position of the surgical instrument's tip.

The centre of the calibrator sphere may be aligned with an axis of the tip of the instrument when placed thereon. Such alignment reduces the number of variables that need to be accounted for when calibrating the position of the tip based on the detected position of the centre of the calibrator. This is turn simplifies the calibration step thus allowing for faster calibration, and equally may improve upon on accuracy and precision of the calibration.

The calibrator may comprise a bore configured to receivingly engage the tip of the surgical instrument. This engagement of the bore with the tip of the surgical instrument may be sufficient to support the calibrator relative to the navigation array in a fixed spatial and angular relationship. As such, there is no requirement for the surgical instrument to be held steady during calibration as the position of the calibrator is fixed relative to both the surgical instrument and the position of the navigation array. The bore may be sized and/or shaped according to the size and/or shape of the tip of the surgical instrument, thus making each calibrator bespoke to each size of surgical instrument to ensure accurate and precise calibration. For instance, where the instrument is coned (e.g. has a coned tip) the bore may be correspondingly cone shaped.

As with prior art arrangements, detection of the calibrator and the navigation array may be based on light, sound waves or magnetic fields. In example embodiments the calibrator and navigation array are optically detectable, more preferably at infrared wavelengths.

The calibrator may comprise an adapter and a reflector connected to one another, the reflector having the circular shape and being optically detectable as the single point in space. In examples where the reflector has a spherical shape, the reflector may be termed a reflector sphere. The adapter may be removably connected to the reflector such that a single reflector can be connected to and removed from a number of different adapters. Similarly, a single adapter can be connected to and removed from a number of different reflectors. The bore may be within the adapter. Thus, the adapter can be tailor-made to the size and shape of the tip instrument. This is particularly advantageous when the reflector and the adapter are removably attached to one another because a single, generic reflector can be used to calibrate a variety of different instruments by connection to a host of different, tailor-made adapters.

The calibrator may additionally comprise a recess that extends along a diameter of the reflector, configured to house a portion of the adapter. This may ensure that the tip of the instrument received within the bore in the adapter is maintained within or at the centre of the reflector so as to allow for the direct detection of the tip as discussed above.

The adapter can optionally comprise a tip portion and an abutting portion of larger cross-sectional area than the tip portion when viewed along a primary axis of the adapter. When the adapter is arranged as such the tip portion can be received within the recess of the reflector, whilst the abutting portion can abut against a surface of the reflector. Such an arrangement can ensure that the tip of the instrument is accurately positioned either at, or at a known displacement from, the centre of the reflector.

Any form of connection means between the adapter and the reflector may be used to ensure sound engagement between the adapter and the reflector, provided the connection means also allows for the adapter to be removed from the reflector. In one example the tip portion of the adapter is provided with a threaded portion, and an internal surface of the recess is provided with a threaded portion that corresponds to the threading on the tip portion. The engagement of these threaded portions provides the required engagement between the adapter and reflector, whilst also allowing the adapter and the reflector to be readily removed from one another.

It is envisioned that the calibrator could be made from any suitable material provided that the calibrator remains detectable as a single point in space. Thus, the calibrator may be plastic or glass, for example. In some cases the calibrator is made from a lightweight material, e.g. plastic. A calibrator made of such a lightweight material helps to prevent damage to the instrument for surgical intervention when the calibrator is placed thereon. Calibrators made from plastic are also advantageously cheap to manufacture and are thus readily replaceable.

The calibrator, the adapter and/or the reflector may be single-use devices intended to be disposed of after use. Each of these components can hence be supplied in sterile packaging and used without any special preparation/sterilisation being required, before being disposed of after calibration. The disposability of the reflector may be particularly advantageous when the adapter is tailor-made based on the surgical instrument and is also designed to be used more than once. In such a case, a single adapter may be used in numerous calibrations of the surgical instrument in conjunction with any number of reflectors being connected thereto. Although the device is designed for use with complex and extensive guided surgery systems, the design of the device does not require any expensive materials or moving parts and it can be made disposable without any disadvantage in relation to costs. The disposability of the calibrator and its constituent components makes it well suited for use in outpatient procedures.

In addition to its use for calibration, the calibrator may also provide advantages in terms of protection to the instrument onto which it is to be placed. The calibrator may thus act as a protective sheath/cover when placed on the tip of the instrument to protect the tip of the instrument from damage and/or to protect an operative from the instrument (e.g. where the instrument comprises a sharp needle).

The calibrator may be placed on the tip on the instrument during or shortly after manufacture of the instrument, optionally by the manufacturer themselves. The instrument may therefore be delivered to an operative with the calibrator already placed as required on the tip of the instrument ready for the step of detecting. This is particularly advantageous where the calibrator acts as a protective sheath since damage to the tip of the instrument may be prevented. In such a scenario, where the instrument is delivered to an operative ready for use with a calibrator already placed on the tip of the instrument, the operative can immediately commence the step detecting of the position of the navigation array and the centre of the calibrator once the instrument is unpackaged.

As with the material of the calibrator, it is envisioned that the calibrator can have any suitable size provided that it remains detectable as a single point in space; however it is preferred that the calibrator has a diameter of less than 30 mm, preferably less than 20 mm, and even further preferably less than 15 mm. For example, the calibrator may be based on an existing sphere for a navigation array, which are known to have diameters or about 11 mm or about 13 mm for two existing products. These relatively small sizes help to ensure that the calibrator remains lightweight and can be handheld. In the case where the calibrator comprises an adapter and a reflector, the reflector may take on these dimensions.

The method of the first aspect may be used to calibrate a variety of surgical instruments, for example, the device described in WO 2014/037524. The surgical instruments that are calibrated by the method of the first aspect may comprise a needle for core needle biopsy, a needle for fine needle biopsy, a trackable needle (e.g. an electromagnetic needle) an electrode for electric or radiofrequency ablation therapy, a cannula for chemical ablative therapy or a neurostimulator.

The navigation array used in the first aspect may be fixedly mounted on the instrument, or it may be integrally formed therewith. Detection of the navigation array may be based on light, sound waves or magnetic fields. Thus, any suitable navigation array can be used. However, for ease of calibration, it is advantageous for the navigation array and the calibrator to be detected in the same way since then only one detection system is needed. Therefore, it is preferable that the navigation array is optically detectable, even more preferably optically detectable at infrared wavelengths. Thus, the navigation array may consist of optically detectable markers such as two dimensional (i.e. flat) or three-dimensional markers.

In one example the navigation array is optically detectable and it comprises reflectors comparable to those described above in relation to the calibrator. This allows for easy detection of the navigation array along with the calibrator. The reflectors may be located in plane with one another and at known irregularly spaced known locations relative to the tip of the instrument. In one preferred embodiment there are at least three reflectors, for example there may be four or five reflectors. The navigation array should be rigidly connected to the surgical instrument since this provides the least risk of inaccuracy and an inadvertent misalignment of the navigation array with the tip of the surgical instrument. Each of the reflectors of the navigation array may be identical to the calibrator.

Certain advantages associated with at least the example embodiments of the present invention are achieved only when the calibrator is a calibrator sphere. These advantages are not necessarily attainable with calibrators of differing circular shapes. For instance, a calibrator sphere is invariant with respect to the direction and orientation from which it is detected. As such, a calibrator sphere can allow for even faster calibration of a surgical instrument as delays associated with achieving the proper alignment and orientation of the tip of a surgical instrument relative to calibration devices that are known from the prior art (e.g. from CN 105919669 A), or indeed with calibrators of the present invention of differing circular shapes, are eliminated.

The present invention also extends to a calibrator used within a method of calibrating an instrument for surgical intervention, such as the method of the first aspect described above. The instrument, as above, has a tip at a distal end thereof and a navigation array spaced from the distal end that is detectable in space, with the navigation array having a fixed spatial and angular relationship with the tip. Thus, according to a second aspect of the invention there is provided a calibrator that is arranged to be placed on the tip of the instrument such that the tip is positioned within the calibrator at a known displacement from the centre of the calibrator, the calibrator having a circular shape and being detectable as a single point in space. The calibrator of the second aspect may be in accordance with any of the relevant features and statements relating to the calibrator in the first aspect discussed above. Thus, many of the advantages provided by the first aspect and second aspect that are discussed above are equally provided by the third aspect of the invention.

Given the unique advantages associated with the calibrator being spherical in shape as outlined above in relation to the first aspect, this concept is regarded as being particularly and independently inventive. Therefore, viewed from a third aspect, there is provided a method of calibrating an instrument for surgical intervention, the instrument having a tip at a distal end thereof and a navigation array spaced from the distal end and being detectable in space, wherein the navigation array has a fixed spatial and angular relationship with the tip. The method comprises the steps of: placing a calibrator sphere on the tip of the instrument such that the tip is positioned at a known displacement from the centre of the calibrator sphere, the calibrator sphere being detectable as a single point in space; detecting the position of the navigation array and the centre of the calibrator sphere; and determining the position of the centre of the calibrator sphere relative to the navigation array, thereby calibrating the position of the tip of the instrument relative to the navigation array. The method of the third aspect may be in accordance with any of the compatible statements discussed above in relation to the first aspect.

In a fourth aspect, the invention also extends to a calibrator sphere used within a method of calibrating an instrument for surgical intervention, such as the method of the third aspect described above. The instrument, as above, has a tip at a distal end thereof and a navigation array spaced from the distal end that is detectable in space, with the navigation array having a fixed spatial and angular relationship with the tip. Thus, according to a fourth aspect of the invention there is provided a calibrator sphere that is arranged to be placed on the tip of the instrument such that the tip is positioned at a known displacement from the centre of the calibrator sphere, the calibrator sphere being detectable as a single point in space. The calibrator sphere of the fourth aspect may be in accordance with any of the relevant features and statements relating to the calibrator sphere discussed above in relation to the other aspects of the invention.

The calibrator of the second and fourth aspects are intended for use in combination with a navigation array and so, viewed from a fifth aspect, the invention provides an apparatus for calibrating an instrument for surgical intervention, the instrument having a tip at a distal end thereof. The apparatus comprises the calibrator as outlined in the second or fourth aspects and a navigation array fixedly mountable to the instrument at a position spaced from the distal end such that the navigation array has a fixed spatial and angular relationship with the tip, wherein the navigation array is detectable in space. The navigation array provided in the fifth aspect may have any of those features of the navigation array described in relation to the first aspect.

The above discussed advantages associated with the calibrator of the second aspect, fourth aspect and/or the apparatus of the fifth aspect are most beneficial in image guided surgical applications. Therefore, in a sixth aspect of the invention there is provided a surgical navigation system comprising the apparatus of the fifth aspect.

The surgical navigation system of the sixth aspect can optionally comprise a computer programme product executable on the surgical navigation system. The computer programme product can contain instructions that when executed will configure the surgical navigation system to detect the position of the navigation array and the centre of the calibrator. The computer programme product can then subsequently determine the position of the centre of the calibrator relative to the navigation array, thereby calibrating the position of the tip of the instrument relative to the navigation array.

The surgical navigation system should comprise means to detect the position of the navigation array and the centre of the calibrator, these means preferably being infrared cameras. Similarly, the surgical navigation system should comprise an output that allows for the navigation array and the centre of the calibrator to be detected. Preferably the output is a light emitting at infrared wavelengths.

The invention also extends to a computer programme product that comprises instructions that, when executed on an appropriate data processor, assist in the method of the first or third aspects. As such, in a seventh aspect of the invention there is provided a computer program product comprising instructions that, when executed on a surgical navigation system, will: detect the position of the navigation array and the centre of the calibrator; and determine the position of the centre of the calibrator relative to the navigation array, thereby calibrating the position of the tip of the instrument relative to the navigation array.

The computer program product of the seventh aspect may be executed on the surgical navigation system of the sixth aspect. Optionally, the computer programme product of the seventh aspect can be used in conjunction with the calibrator of the second aspect, the calibrator sphere of the fourth aspect and/or the apparatus of the fifth aspect.

In an eighth aspect of the invention, there is also provided a kit comprising a calibrator as defined in any of the preceding statements and an instrument for surgical intervention, the instrument having a tip at a distal end thereof and a navigation array, or a mounting for a navigation array, spaced from the distal end and being detectable in space. The instrument may be in accordance with the instrument(s) defined above.

Certain preferred embodiments of the invention will now be described by way of example only and with reference to the accompanying drawings in which.

Figure 1:
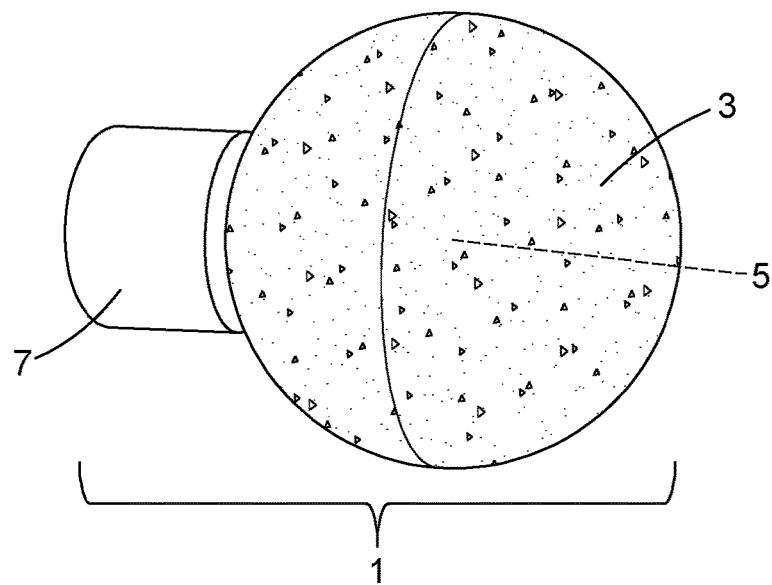
FIG. 1 shows a calibrator in accordance with an embodiment of the present invention.
Figure 2:
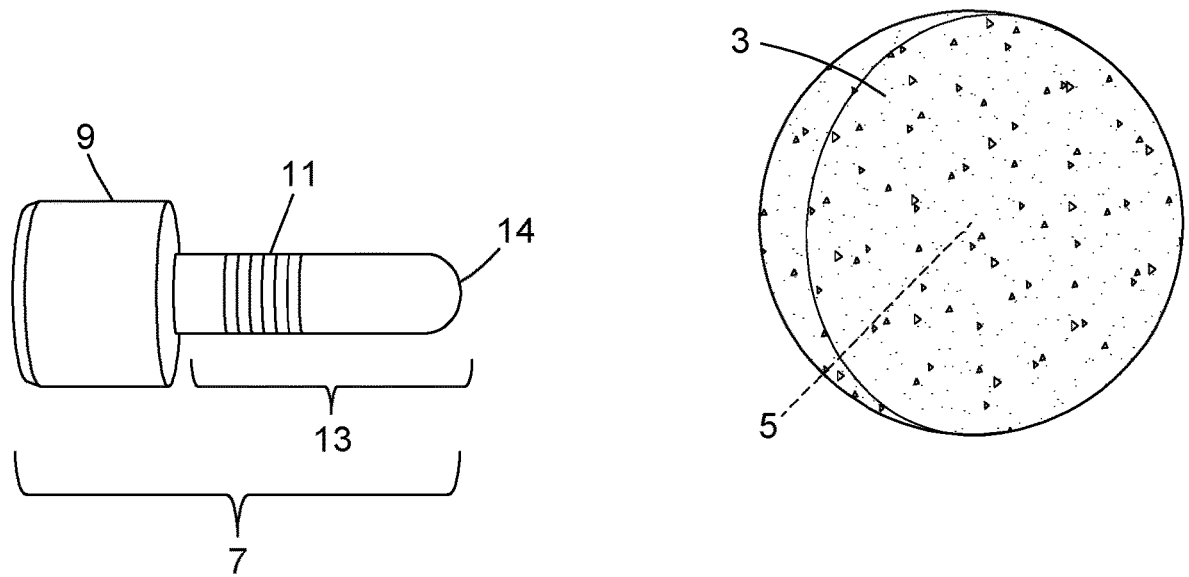
FIG. 2 shows the calibrator of FIG. 1 disassembled into its component parts.

FIG. 1 shows a calibrator 1, more specifically a calibrator sphere 1. The calibrator sphere 1 is suitable for calibrating the position of a tip of an instrument for surgical intervention. The calibrator sphere 1 comprises a reflector sphere 3 and an adapter 7. The reflector sphere 3 has a centre 5 and a recess (not shown) that extends partially along a diameter of the reflector sphere 3 to a distance just beyond the centre 5. The recess is configured to receive a tip portion 13 (see FIG. 2) of the adapter 7. A portion of the internal surface of the recess that is closest to the surface of the sphere 3 is female threaded. The reflector sphere 3 can reflect electromagnetic radiation, specifically at infrared wavelengths such that a position of the centre 5 of the reflector sphere 3 can be located in space.

The adapter 7 comprises an abutting portion 9 adjacent to the tip portion 13 of larger cross-sectional area than the tip portion 13 when viewed along the primary axis of the adapter 7. The abutting portion 9 of the adapter 7 is at a fixed distance from a tip 14 of the tip portion 13. A portion 11 of the tip portion 13 positioned toward the abutting portion 9 is male threaded. The female threading within the recess of the reflector sphere 3 corresponds to the male threading on the portion 11. A bore (not shown) extends along a primary axis of the adapter 7, through an entire length of the abutting portion and into a tip portion, terminating at a position just short of the tip 14. The bore is configured to receive a tip of an instrument for surgical intervention, specifically the tip 21 of the instrument 15 depicted in FIGS. 3 and 4. Thus, the size of the bore corresponds to the dimensions of the tip 21 of the surgical instrument 15 as depicted in FIG. 3.

As shown in FIG. 1, the adapter 7 is configured to be partially inserted into the reflector sphere 3, such that the tip portion 13 is housed within the recess of the reflector sphere 3 and a surface of the abutting portion 9 adjacent to the tip portion 13 abuts a surface of the reflector sphere 3. In this configuration, the termination point of the bore within the adapter 7 is positioned exactly at the centre of the reflector sphere 3. This partially inserted configuration as depicted in FIG. 1 is maintained through the engagement of the male threaded portion 11 with the correspondingly female threaded portion of the recess in the reflector sphere 3. This engagement ensures that the adapter 7 and the sphere 3 can be fixedly attached to one another, and hence the position of the termination point of the bore can be fixedly maintained at the centre 5 of the reflector sphere 3. This threaded engagement also ensures that the reflector sphere 3 and the adapter 7 can be readily separated from one another such that the sphere 3 can be used in conjunction with a plurality of different adapters 7, and vice versa.

Figure 3:
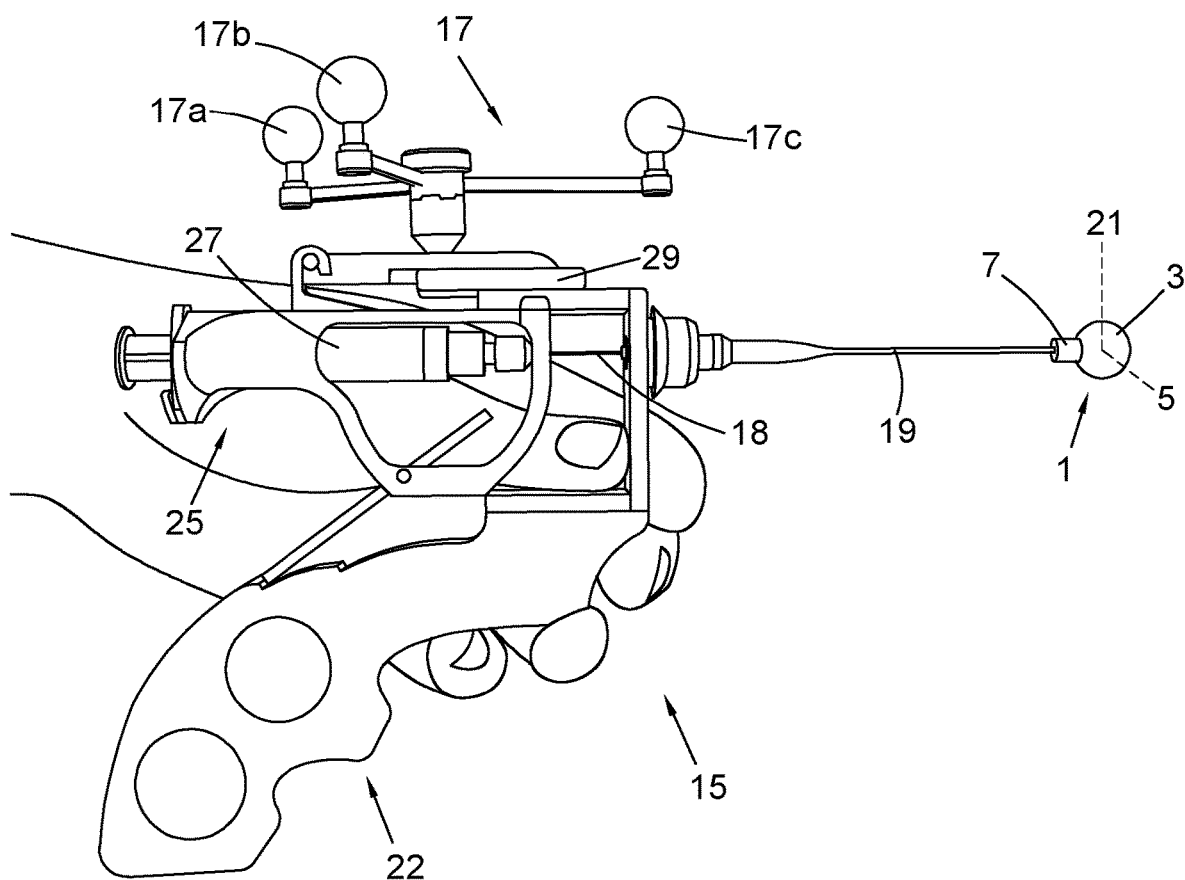
FIG. 3 shows a side view of an instrument for surgical intervention with the calibrator of FIG. 1 mounted on a tip of the instrument.
Figure 4:
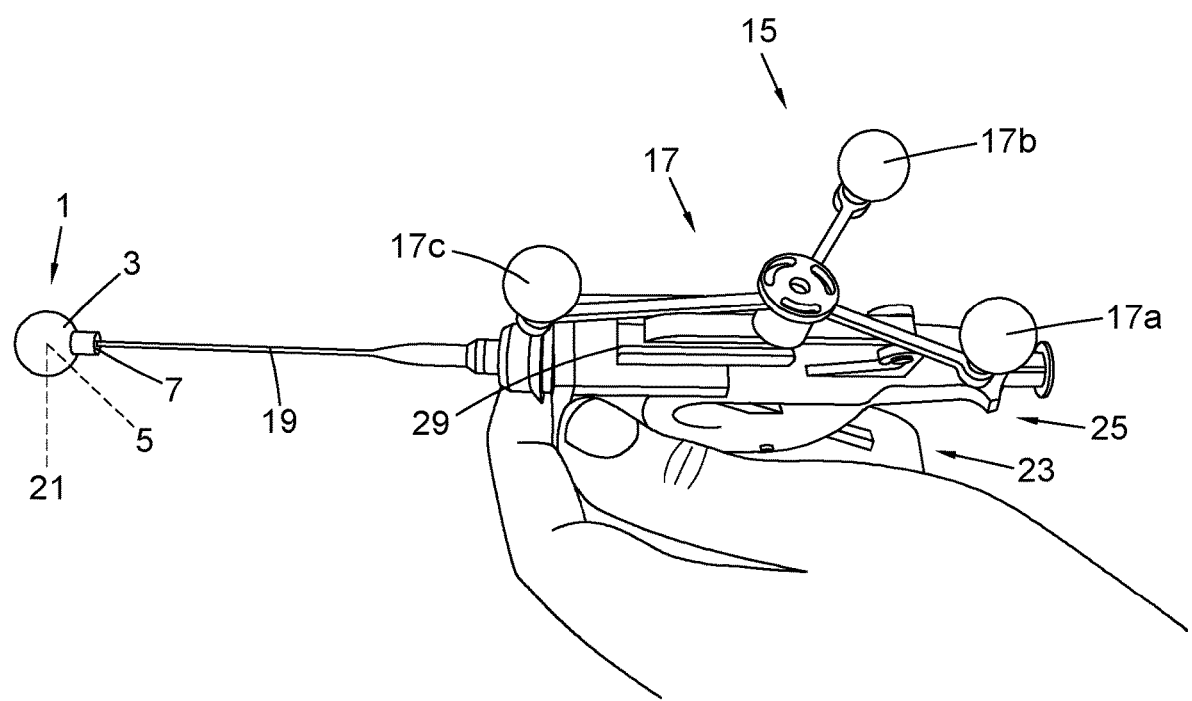
FIG. 4 shows a top view of the instrument for surgical intervention as depicted in FIG. 3 with the calibrator of FIG. 1 mounted on a tip of the instrument for surgical intervention.

As shown in FIGS. 3 and 4, the calibrator sphere 1 is configured to be placed on the tip 21 of an instrument 15 for surgical intervention to allow for calibration of said instrument 15. It will be recognised that whilst the calibrator sphere 1 is described herein in relation to a specific instrument 15 as depicted in FIGS. 3 and 4, the calibrator sphere 1 can suitably be used to calibrate the position of the tip of a variety of other instruments.

The calibrator sphere 1 is placed on the tip of a rigid lumen 19 of the instrument 15 such that the tip of the rigid lumen 19 is positioned at the termination of the bore within the adapter 7, and is thus at the centre 5 of reflector sphere 3. The lumen 19 houses a needle 18, with the tip 21 of the needle 18 axially aligning with the tip of the lumen 19 in the configuration depicted in FIGS. 3 and 4.

The instrument comprises a body 23 and a proximal piece 25 slidably mounted on the body 23. The proximal piece 25 has the needle 18 mounted thereon such that the position of the proximal piece 25 and the needle 18 are fixed relative to one another, whilst the needle 18 and the body 23 are movable relative to one another. The body 23 has the rigid lumen 19 fixedly mounted thereon such that the lumen 19 is fixed relative to a position of the body 23 and houses the needle 18 in a slidably movable manner. The instrument 15 also has a syringe 27 connected to the needle 18 via the proximal piece 25. The syringe 27 can be coupled to the needle 18 using any suitable coupling mechanism.

The proximal piece 25 comprises a navigation array 17 fixedly mounted thereon that comprises three reflector spheres 17*a*; 17*b*; 17*c* fixedly positioned relative to one another in an irregular manner. The navigation array 17, through detection of the position of the centre of reflector spheres 17*a*; 17*b*; 17*c*, can allow for the position of the instrument 15 to be located, specifically the tip 21 of the instrument 15 by a surgical navigation system after it has been calibrated with the tip 21.

The instrument 15 further includes a track 29 on the body section 23 in which the navigation array 17 is slidably mounted. The track 29 allows the navigation array 17 to slide along the body 23 in a manner that corresponds to the slide of the proximal piece 25 along the body 23. As such, the proximal piece 25, navigation array 17 and needle 18 can be slid relative to both the body 23 and the rigid lumen 19 along a primary axis of the instrument 15, whilst remaining in a fixed position relative to one another. Thus, though not depicted in the Figures, the tip 21 of the needle 18 can be slid to protrude from the tip of the rigid lumen 19.

Given that the position of the proximal piece 25 and the needle 18 are fixed relative to one another, the position of the navigation array 17 can always be relied upon to indicate a position of the tip 21 of needle 18 once the position of the tip 21 of the needle 18 has been calibrated relative to the navigation array 17.

The calibration of the instrument 15, specifically the calibration of the relative positions of the navigation array 17 and the tip 21 of the needle 18 commences by placing calibrator sphere 1 on the tip of the lumen 19 via insertion of the tip 21 through the bore of the adapter 7 until such a time as the tip of the lumen 19 is positioned at the termination point of the bore as is depicted in FIGS. 3 and 4. Given that calibration of the instrument 15 takes place when the tip 21 of needle 18 is axially aligned with the tip of the lumen 19, the tip 21 will also be positioned at the termination point of the bore. At this time, the adapter 7 will be engaged with the tip of the lumen 19 so as to removably secure the calibrator sphere 1 in place on the lumen 19, and the tip 21 of needle 18 will be positioned at the centre 5 of calibrator sphere 3.

Once the calibrator sphere 1 is positioned on the instrument 15 such that the tip 21 of the needle is positioned at the centre 5 of the reflector sphere 3, the position of the navigation array 17, specifically the centre of each of the reflector spheres 17a; 17b; 17c and the centre 5 of the reflector sphere 3 are detected. The detection is carried out by a surgical navigation system. The surgical navigation system comprises a light source that emits light in the infrared in the general direction of the reflector sphere 3 and the navigation array 17. An infrared camera is also disposed within the surgical navigation system that detects infrared radiation that is reflected by the centre of each reflector spheres 17a; 17b; 17c and the centre of the reflector sphere 3. The reflected infrared radiation detected by the infrared camera is indicative of the position the centre of each of the reflector spheres 17a; 17b; 17c on the navigation array 17 and of the centre 5 of the reflector sphere 3 (and hence the tip 21 of the surgical instrument). Software comprised within the surgical navigation system enables the conversion of the detected reflected infrared radiation into the position of the centre of each of the reflector spheres 17a; 17b; 17c and the centre 5 of the reflector sphere 3.

Once the surgical navigation system has detected the position of the centre of each of the reflector spheres 17a; 17b; 17c and the centre 5 of the reflector sphere 3, the software comprised within the surgical navigation system enables the surgical navigation system to determine the position of the centre 5 of the reflector sphere 3 relative to the optically detectable spheres 17a; 17b; 17c on the navigation array 17. Thus, as the position of the centre 5 of the reflector sphere 3 relative to the navigation array 17 is known to the surgical navigation system, the position of the tip 21 of the instrument 15 is also known, and the tip 21 of the surgical instrument 15 is hence calibrated relative to the position of the navigation array 17.

Thus, when the calibrator sphere 1 is removed from the tip 21 of the instrument 15 the position of the tip 21 is still known to the surgical navigation system through detection of the navigation array 17. The software in the surgical navigation system enables continued tracking and detection of the navigation array 17 once the calibrator sphere 1 has been removed, and thus the position of the tip 21 of the instrument 15 can be continually calculated by the surgical navigation system. As such, even when the instrument 15 is in use and the tip 21 of the needle 18 is made to protrude from the tip of the rigid lumen 19 into the desired site within the patient through movement of the proximal piece 25 relative to the body section 23, the position of the tip is still known to the surgical navigation system. The software within the surgical navigation system enables the position of the tip 21 of the surgical instrument 15 to be visually output to the user on a liquid crystal display, thus enabling the user to orient and position the instrument 15 in order to place the tip 21 in the desired site in the patient when the instrument 15 is in use.

In alternative examples, which are not shown in the Figures, the spherical reflectors may be replaced by circular or cylindrical markers. Thus, the calibrator used at the tip of the instrument may be replaced by a circular or cylindrical marker and/or the navigation array may make use of circular or cylindrical markers in place of spheres.

The invention claimed is:

1. A method of calibrating an instrument for surgical intervention, the instrument having a tip at a distal end thereof and a navigation array spaced from the distal end and configured to be detected in space, wherein the navigation array has a fixed spatial and angular relationship with the tip, the method comprising the steps of:
    placing a calibrator having a spherical shape on the tip of the instrument such that the tip is positioned within the spherical shape at a known displacement from a center of the spherically shaped calibrator, the center of the calibrator configured to be detected as a single point in space, the calibrator configured such that the known displacement can be zero;
    detecting a position of the navigation array and the center of the calibrator; and
    determining a position of the center of the calibrator relative to the navigation array, thereby calibrating a position of the tip of the instrument relative to the navigation array.

2. The method of claim 1, wherein the tip is positioned at the center of the calibrator.

3. The method of claim 1, wherein the calibrator and the navigation array are optically detectable.

4. The method of claim 1, wherein the calibrator is a single-use device intended to be disposed of after use.

5. The method of claim 1, wherein the calibrator comprises a bore, the bore being configured to receive the tip of the surgical instrument.

6. The method of claim 1, wherein the calibrator comprises an adapter attached to a reflector, the reflector having the spherical shape.

7. The method of claim 5, wherein the calibrator comprises an adapter attached to a reflector, the reflector having the spherical shape, and wherein the adapter comprises the bore.

8. The method of claim 6, wherein the adapter is removably attached to the reflector.

9. The method of claim 6, wherein the reflector comprises a recess extending along a diameter thereof, the recess being configured to at least partially receive the adapter.

10. The method of claim 9, wherein the adapter comprises a tip portion and an abutting portion of larger cross-sectional area than the tip portion when viewed along a primary axis of the adapter, and the tip portion is configured to be received within the recess such that a surface of the reflector abuts against the abutting portion.

11. The method of claim 10, wherein a portion of the tip portion is threaded,
    wherein an internal surface of the recess is threaded in a manner corresponding to the threading on the tip portion, and
    wherein placing a calibrator having a spherical shape on the tip of the instrument comprises rotating the tip portion such that the threaded portion of the tip portion engages the threaded internal surface of the recess.

12. The method of claim 6, wherein the adapter and/or the reflector are single-use devices intended to be disposed of after use.

13. The method of claim 1, wherein the calibrator acts as a protective sheath to prevent damage to and/or bending of the instrument after being placed on the tip of the instrument.

14. A calibrator for use in a method of calibrating an instrument for surgical intervention, the instrument having a tip at a distal end thereof and a navigation array spaced from the distal end and configured to be detected in space, the navigation array having a fixed spatial and angular relationship with the tip, wherein the calibrator has a spherical shape and is arranged to be placed on the tip of the instrument such that the tip is positioned within the spherical shape at a known displacement from a center of the spherically shaped calibrator, the center of the calibrator is configured to be detected as a single point in space, and the calibrator is configured such that the known displacement can be zero.

15. The calibrator of claim 14, wherein the calibrator is configured to receive the tip of the instrument at the center of the calibrator.

16. The calibrator of claim 14 manufactured from plastic.

17. The calibrator of claim 14, wherein the calibrator is a single use device intended to be disposed of after use.

18. The calibrator of claim 14, wherein the calibrator is optically detectable.

19. The calibrator of claim 14, wherein the calibrator acts as a protective sheath to prevent damage to and/or bending of the instrument when placed on the tip of the instrument.

20. An apparatus for calibrating an instrument for surgical intervention, the instrument having a tip at a distal end thereof, the apparatus comprising:
  a calibrator as claimed in claim 14,
  wherein the navigation array is configured to be fixedly mounted to the instrument at a position spaced from the distal end such that the navigation array has a fixed spatial and angular relationship with the tip, and wherein the navigation array is configured to be detected in space.

21. A surgical navigation system comprising the apparatus of claim 20.

22. The surgical navigation system of claim 21, comprising a computer program product executable on the surgical navigation system, wherein the computer program product contains instructions that when executed will configure the surgical navigation system to detect the position of the navigation array and the center of the calibrator, and subsequently determine the position of the center of the calibrator relative to the navigation array, thereby calibrating the position of the tip of the instrument relative to the navigation array.

23. A computer program product comprising instructions for execution on the surgical navigation system of claim 21, the surgical navigation system including hardware or software connections that allows for the detection and subsequent calibration of the calibrator and the navigation array;
  wherein after the calibrator is placed on the tip of the instrument such that the tip is positioned within the calibrator at a known displacement from the center of the calibrator, the instructions, when executed, will configure the surgical navigation system to:
    detect the position of the navigation array and the center of the calibrator; and
    determine the position of the center of the calibrator relative to the navigation array, thereby calibrating the position of the tip of the instrument relative to the navigation array.

24. A kit comprising a calibrator as defined in claim 14 and an instrument for surgical intervention, the instrument having a tip at a distal end thereof, wherein the navigation array, or a mounting for the navigation array, is spaced from the distal end and is configured to be detected in space.

* * * * *